United States Patent [19]
Parshad et al.

[11] Patent Number: 6,017,706
[45] Date of Patent: Jan. 25, 2000

[54] PROCESS FOR IDENTIFYING COMPOUNDS WHICH PROTECT AGAINST THE FORMATION OF FLUORESCENT LIGHT INDUCED DNA LESIONS AND X-RAY-INDUCED LESIONS

[75] Inventors: Ram Parshad, Olney, Md.; Katherine K. Sanford-Mifflin, Dover, Del.; Jay H. Robbins, Potomac; Charles W. Boone, Bethesda, both of Md.

[73] Assignee: The United States of America as represented by the Department of Health and Human Services, Washington, D.C.

[21] Appl. No.: 08/852,355

[22] Filed: May 7, 1997

Related U.S. Application Data

[63] Continuation-in-part of application No. 08/611,330, Mar. 8, 1996, Pat. No. 5,773,219, which is a continuation-in-part of application No. 08/228,825, Apr. 18, 1994, abandoned, which is a continuation-in-part of application No. 07/957,315, Oct. 6, 1992, abandoned.

[51] Int. Cl.$^7$ .................................................. C12Q 1/68
[52] U.S. Cl. .............................. 435/6; 435/34; 436/811
[58] Field of Search ................................ 435/6, 29, 34; 424/3; 436/64, 811; 935/77

[56] References Cited

U.S. PATENT DOCUMENTS

| | | | |
|---|---|---|---|
| 4,933,274 | 6/1990 | Sanford et al. | 435/6 |
| 4,975,365 | 12/1990 | Grossman et al. | 435/6 |
| 5,482,833 | 1/1996 | Pero et al. | 435/6 |
| 5,641,754 | 6/1997 | Iversen | 514/44 |
| 5,773,219 | 6/1998 | Sanford-Mifflin et al. | 435/6 |

OTHER PUBLICATIONS

Parshad, R., Price, F. Tarone, R.J. Robbins and Sanford, K.K. (1991) "Cytogenetic evidence of a cell–cycle–dependent DNA repair deficiency: A possible diagnostic feature of Alzheimer Disease." Proceedings of the 8th International Congress of Human Genetics, Oct. 6–11, 1991, Washington, D.C. U.S.A., Am. J. Human Genetics Suppl. 49, 155. Abstract.

Chen, P., et al., "Heterogeneity in Alzheimer's disease: evidence from cellular radiosensitivity and complementation of this phenotype", Mutation Res. (1991) 256, 21–7.

Tobi, S.E., et al. "Chromosomal radiosensitivity of lymphocytes from Alzheimer's disease patents", J. Med. Genet. (1990) 437–40.

Parshad, R., et al., "Susceptibility to fluorescent light–induced chromatid breaks associated with DNA repair deficiency and malignant transformation in culture", Cancer Res. (1980) 40, 4415–9.

Price, F.M., et al., "Radiation–induced chromatid aberrations in Cockayne syndrome and xeroderma pigmentosum group C fibroblasts in relation to cancer predisposition", Cancer Genet. Cytogenet. (1991) 57, 1–10.

Sanford, K.K., et al., "Responses of human cells in culture to hydrogen peroxide and related free radicals generated by visible light: relationship to cancer susceptiblity", in *Free Radicals, Aging, and Degenerative Diseases*, edited by Johnson, J.E., et al., Alan R. Liss, Inc., New York, 1986, pp. 373–394.

Sanford, K.K., et al., "Role of DNA repair in malignant neoplastic transformation of human mammary epithelial cells in culture", Carcinogenesis (1992) 13, 1137–41.

Parshad, R., et al., "Neoplastic Transformation of human cells in culture associated with deficient repair of light–induced chromosomal DNA damage", Int. J. Cancer: 30, 153–159 (1982).

Parshad, R., et al., "Chromatid damage induced by fluorescent light during $G_2$ phase in normal and Gardner Syndrome fibroblasts," Interpretation in terms of deficient DNA repair, Mutation Research, 151 (1985) 57–63.

Gantt R., et al., "Enhanced $G_2$ chromatid radiosensitivity, an early stage in the neoplastic transformation of human epidermal keratinocytes in culture", Cancer Research 47, 1390–1397 (1987).

Parshad, R., et al., A DNA–Repair Defect In Alzheimer Disease, vol. 42, No. 1, 98A (1994) (Abstracts Submitted to the Annual Meeting of the Western Section of the American Federation for Clinical Research held Feb. 9–12, (1994) (published after filing date of first priority application) Abstract.

Melnick, L., et al., "Defective DNA Repair In Alzheimer Disease: Use In A Predictive Test On Cultured Cell Lines", Clinical Research vol. 42, No. 3, 464A (Oct. 1994) (published after filing dates of first two priority applications) Ab.

Parshad, R., et al., "Defective DNA Repair In Sporadic, Familial, And Down–Syndrome Alzheimer Disease", Journal of Investigative Medicine, vol. 43 (Supplement 2), 415A (Apr. 1995) (published after filing dates of first two priority applications).

(List continued on next page.)

*Primary Examiner*—Ralph Gitomer
*Attorney, Agent, or Firm*—Morgan & Finnegan, LLP

[57] ABSTRACT

Processes for detecting compounds which protect against fluorescent light-induced DNA lesions, in particular DNA lesions which are induced by oxygen free radicals, are disclosed. The methods of the present invention encompass modifying $G_1$-phase test and/or $G_2$-phase tests so that a compound which is suspected of being capable of protecting against the formation of fluorescent light-induced DNA lesions (i.e., a suspected "DNA protectant"), such as an anti-oxidant or free-radical scavenger, is added to the cell cultures prior to irradiation of the cell cultures with fluorescent light or x-rays. Addition of a DNA protectant to cultures of human skin fibroblasts or PHA-stimulated blood lymphocytes significantly reduces the frequency of radiation-induced chromatid breaks so that there is a small, preferably no, statistical difference in the frequency of radiation-induced chromatid breaks in Alzheimer disease cells in the presence or absence of caffeine in the $G_1$-phase test using fluorescent light, or in normal cells in the presence or absence of ara-C in the $G_2$-phase test using fluorescent light or x-rays.

34 Claims, No Drawings

OTHER PUBLICATIONS

Melnick, L.K., et al., "Xeroderma Pigmentosum Group–A And Alzheimer Disease Cells Have Similar Defective Repair of Fluorescent Light–Induced DNA Damage", Journal of Investigative Medicine, vol. 43 (Supplement 3), 508A, (Sep. 1995) (published after filing dates of first two priority applications).

Backon, J., "Dementia in Cancer Patients Undergoing Chemotherapy: Implication of Free Radical Injury and Relevance to Alzheimer Disease", Medical Hypotheses, 35, 146–147 (1991).

Parshad, R., Sanford, K.K., Price. F.M., Melnick, L.K., Nee, L.E., Schapiro, M.B., Tarone, R.E. and Robbins, J.H. "Fluorescent light–induced chromatid breaks distinguish Alzheimer disease cells from normal cells in tissue culture", Proc. Natl. Acad. Sci., USA 93, 5146–5150 (May 1996) (published after the filing dates of the three priority applications). "Paradigm of DNA–Repair Disease, Points To Alzheimer's Diagnosis, Therapy", *BioWorld Today*, vol. 7, No. 102, 1–2, (May 23, 1996) (published after the filing dates of the three priority applications).

Parshad R., Neoplastic Transformation of Human Cells in Culture Associated with Deficient Repair of Light Induced Chromosomal DNA Damage, Int J Cancer 30 153–159, 1982.

Pincheira J., G2 Repair and Evaluation of the Cytogenetic Damage Induced by Low Doses of X–Irradiation During G0 in Human Lymphocytes, Biol Res 28(4):267–275, 1995.

Parchad R., Fluorescent Light–Induced Chromatid Breaks Distinguish Alzheimer Disease Cells From Normal Cells in Tissue Culture, Proc. Natl. Acad. Sci. USA 93:51466–5150, May 1996.

Antoccia A., Chromosomal Sensitivity to Clastogenic Agents and Cell Cycle Perturbations in Nijmegen Breakage Syndrome Lymphoblastoid Cell Lines, Int J Radiat Biol 71(1):41–49, 1997.

PROCESS FOR IDENTIFYING COMPOUNDS WHICH PROTECT AGAINST THE FORMATION OF FLUORESCENT LIGHT INDUCED DNA LESIONS AND X-RAY-INDUCED LESIONS

RELATED APPLICATIONS

This application is a continuation-in-part of U.S. application Ser. No. 08/611,330, filed Mar. 8, 1996, which issued as U.S. Pat. No. 5,773,219 on Jun. 30, 1998, which application is in turn a continuation in part of U.S. application Ser. No. 08/228,825, filed Apr. 18, 1994, now abandoned which is in turn a continuation-in-part of U.S. application Ser. No. 07/957,315, filed Oct. 6, 1992, now abandoned.

FIELD OF THE INVENTION

This invention relates to methods for identifying compounds which protect against the formation of DNA lesions which are induced by free radicals. In particular, these methods are directed to an in vitro cell assay for the identification of compounds that protect against DNA lesions introduced through x-rays or fluorescent light.

A $G_2$-phase test using x-rays or fluorescent light is described in U.S. Pat. No. 4,933,274, issued to Sanford, K. K., Parshad, R., and Jones G. M., entitled "Process for Detecting Genetic Susceptibility to Cancer". This method describes a $G_2$-phase test using x-rays or fluorescent light to damage fibroblasts or peripheral blood lymphocytes for distinguishing cells of individuals susceptible to cancer from cells of normal individuals.

A $G_1$-phase test and a $G_2$-phase test using fluorescent light are described in U.S. application Ser. No. 08/611,330 (35) and also in Parshad et al. (1996) (36). Cells from Alzheimer disease (AD) patients and normal individuals behave significantly differently in these tests, and, therefore, these tests aid in the diagnosis of AD in a patient (35, 36).

The methods of the present invention encompass modifying the above-mentioned $G_1$-phase test and/or $G_2$-phase tests, so that a compound which is suspected of being capable of protecting against the formation of induced DNA lesions (i.e., a suspected "DNA protectant"), is added to the cell cultures prior to irradiation of the cell cultures with either fluorescent light or x-rays. Addition of a DNA protectant to cultures of human skin fibroblasts or PHA-stimulated blood lymphocytes significantly reduces the frequency of induced chromatid breaks (CBs) so that there is a small, preferably no, statistical difference in the frequency of induced chromatid breaks in AD cells in the presence or absence of caffeine in the $G_1$-phase test, or in normal cells in the presence or absence of ara-C in the $G_2$-phase test.

Some advantages of the present invention include 1) the identification of compounds useful for inhibiting or preventing free radical-induced DNA damage; 2) the identification of compounds potentially useful for medical treatments or protocols designed to slow, alleviate, or prevent altogether the neurodegeneration of AD, which may in turn lead to methods to delay or prevent the clinical onset of AD; 3) to study and understand how defective DNA repair is involved in the cause and/or pathophysiology of AD, 4) the identification of compounds potentially useful for preventing or blocking the carcinogenic process in humans and which are, therefore, potentially useful in preventing or delaying carcinoma onset; and 5) the identification of compounds potentially useful for treatments or protocols designed to act as chemoprotectants.

Abbreviations: AD, Alzheimer disease; ara-C, β-cytosine arabinoside; CB, chromatid break; CBF, CB frequency (i.e., number of CBs per 100 metaphase cells); DS, Down syndrome; FL, fluorescent light; NER, nucleotide excision repair; TFM, theaflavin mixture; XP, xeroderma pigmentosum; XP-A, XP complementation group A.

Note: In the present application, both the term "chromatid breaks" (also known as displaced breaks) and "chromatid gaps" (also known as non-displaced breaks) are referred to as "chromatid breaks", except where otherwise indicated. Thus, the term CBF, used herein, replaces the terms "chromatid aberration index (CAI)" and "frequencies of chromatid aberrations (CA)", which were used in U.S. application Ser. No. 08/611,330, filed Mar. 8, 1996. In that application, CAI was defined as "the total number of chromatid breaks plus gaps per 100 metaphase cells."

BACKGROUND OF THE INVENTION

Elaborate repair mechanisms evolved to maintain integrity of DNA, and their defects result in a variety of disorders (1–7). Inherited defects in nucleotide excision repair (NER) cause neurodegeneration, as in xeroderma pigmentosum (XP) (1–7), an autosomal recessive disease with defective NER of 254-nm UV-induced (1–7), as well as oxygen free radical-induced (7), DNA lesions. Efficient repair of vital genes in postmitotic neurons is essential to maintain the nervous system, for such neurons cannot be replaced. Defective repair presumably kills XP neurons via lethal accumulation of unrepaired, free radical-induced DNA lesions (5–7).

Neurodegeneration and amyloid deposition occur in familial and sporadic AD and in all patients with trisomy-21 Down syndrome (DS) (4). AD(8) and DS(9) cells have normal survival after exposure to 254-nm UV radiation. AD cells have normal UV-induced unscheduled DNA synthesis in the genome overall (10) and normal removal of UV-induced pyrimidine dimers from transcribing genes (11). But AD and DS cells respond abnormally to the ionizing radiation-type of DNA damage in cell-survival (8, 10–12), chromatid-aberration (13–15), and alkaline-elution (10, 12) assays that are dependent on DNA repair (1, 8, 10–15). However, these assays show abnormalities too small to be diagnostically useful.

$G_1$-and $G_2$-phase tests which readily distinguish AD from normal cells are described in U.S. application Ser. No. 08/611,330 (35) and also in Parshad et al. (1996) (36). The disclosure of these documents are incorporated by reference herein. In these tests, asynchronously dividing cells are irradiated with fluorescent light. To inhibit DNA repair or processing of radiation-induced DNA damage, either β-cytosine arabinoside (ara-C) for the $G_2$-phase test or caffeine for the $G_1$-phase test, are added and chromatid breaks arising at the next metaphase (15–17) are quantified. By arresting metaphase cells with colcemid for 1 h starting at either 0.5 h or 14–18 h postirradiation, cells that had been in either the $G_2$ or $G_1$ phase of the cell cycle, respectively, when irradiation ended (18) are evaluated. In the $G_1$-phase test using fluorescent light, the presence of a significant increase in the amount of chromatid damage in the irradiated cell cultures to which caffeine was added, as compared to the amount of chromatid damage observed in the irradiated cell cultures to which caffeine was not added, aids in the diagnosis of AD in a patient suspected of having AD. In contrast, in the $G_1$-phase test using fluorescent light, in normal cells there is no significant difference in the amount of chromatid damage in the irradiated cell cultures in the presence or absence of caffeine. (35, 36).

In the $G_2$-phase test using fluorescent light, the absence of a significant increase of at least 15 breaks per 100 metaphase cells in the amount of chromatid damage in the irradiated cell cultures to which ara-C was added, as compared to the amount of chromatid damage observed in the irradiated cell cultures to which ara-C was not added, aids in the diagnosis of AD in the patient suspected of having AD. In contrast, in the $G_2$-phase test using fluorescent light, in normal cells there is a significant increase in the amount of chromatid damage in the irradiated cell cultures in the presence of ara-C as compared to the amount of chromatid damage in the absence of ara-C. (35, 36).

The $G_2$-phase test is also the subject of U.S. Pat. No. 4,933,274, issued to Sanford, K. K., Parshad, R., and Jones, G. M., entitled "Process for Detecting Genetic Susceptibility to Cancer". This patent describes a $G_2$-phase test using either X-rays or fluorescent light to damage fibroblasts or peripheral blood lymphocytes for distinguishing cells of individuals susceptible to cancer from cells of normal individuals. The disclosure of this patent is incorporated by reference herein.

The DNA repair mechanism responsible for the repair of DNA lesions produced by the x-rays in the $G_2$-phase test are different from the DNA repair mechanism responsible for the DNA lesions produced in the $G_1$-phase with caffeine and the $G_2$-phase test with ara-C. The methods described herein provide a means for identifying those compounds with anti-oxidant properties or free radical scavenger properties capable of ameliorating or preventing the free radical damage responsible for the onset of cancer or responsible for amelioration or preventing neurodegenerative diseases, such as Alzheimer disease.

SUMMARY OF THE INVENTION

This invention relates to methods for identifying compounds which protect against the formation of DNA lesions which are induced by free radicals. In particular, these methods are directed to an in vitro cell assay for the identification of compounds that protect against DNA lesions introduced through x-rays or fluorescent light.

One embodiment of the invention is based on the cytogenetic response of cultured cells to fluorescent light, in the presence and absence of a DNA repair inhibitor during the post-exposure period. The $G_1$-phase test and the $G_2$-phase test using fluorescent light are described in U.S. application Ser. No. 08/611,330 (35) and also in Parshad et al. (1996) (36). Cells from Alzheimer disease patients and normal individuals behave significantly differently in these tests (35, 36). The methods of the present invention encompass modifying the $G_1$-phase test and/or $G_2$-phase test, so that a compound which is suspected of being capable of protecting against the formation of fluorescent light-induced DNA lesions (i.e., a suspected "DNA protectant"), such as an anti-oxidant or free-radical scavenger, is added to the cell cultures prior to irradiation of the cell cultures with fluorescent light. Addition of a DNA protectant to cultures of human skin fibroblasts or PHA-stimulated blood lymphocytes significantly reduces the frequency of radiation-induced chromatid breaks so that there is a small, preferably no, statistical difference in the frequency of radiation-induced chromatid breaks in AD cells in the presence or absence of caffeine in the $G_1$-phase test, or in normal cells in the presence or absence of ara-C in the $G_2$-phase test.

A further embodiment of this invention is based on the cytogenetic response of cultured cells to x-rays during the post-exposure period. The $G_2$-phase test using x-rays is described in U.S. Pat. No. 5,933,274. The methods of the present invention encompass modifying the $G_2$-phase test, so that a compound (or composition of compounds) suspected of being capable of protecting against the formation of x-ray induced DNA lesions, such as an anti-oxidant or free-radical scavenger, is added to the cell culture prior to irradiation of the cell cultures with x-rays.

The methods of the invention are envisioned as being particularly useful in aiding or assisting in the selection of compounds which will be useful in ameliorating, preventing or treating Alzheimer disease (AD) in a human subject, or will be useful as chemoprotective compounds in ameliorating, preventing or treating cancers in a human subject.

The invention comprises assays, and kits formed therewith, with which to test for compounds which protect against the formation of induced DNA lesions, preferably oxygen free radical-induced DNA lesions, by statistical comparison of chromatid break and gap frequency arising in skin fibroblasts or peripheral blood lymphocytes.

DETAILED DESCRIPTION OF THE INVENTION

Exposure of human cells in culture to fluorescent light produces several DNA lesions, including strand breaks and base damage. The breaks, together with indirect breaks formed during repair of base damage, are quantified as chromatid breaks at the subsequent metaphase. When exposed during $G_1$ phase, skin fibroblasts from patients with AD have similar CBFs as fibroblasts from age-matched normal donors. However, addition of caffeine during the S-phase following $G_1$ light exposure significantly increases CBFs only in cells of people who either have AD, are destined to develop AD, or are at risk to develop AD. These results suggest that damage is repaired in normal cells during $G_1$ phase but persists in cells of people who either have AD, are destined to develop AD, or are at risk to develop AD. During S phase, the unrepaired lesions cause spaces to form in newly synthesized DNA and these spaces are kept open when caffeine is present. Addition of ara-C, an inhibitor of DNA repair synthesis, to cells after $G_2$ light exposure significantly increases CBs in the normal cells, but not the cells of people who either have AD, are destined to develop AD, or are at risk to develop AD, indicating that normal, but not AD or AD susceptible cells, have incision activity for removal of base damage during $G_2$. From these results it is inferred that lesions persist in cells of people who either have AD, are destined to develop AD, or are at risk to develop AD during $G_1$ and $G_2$ and that the premature death of postmitotic neurons in AD may be caused by accumulation of unrepaired DNA lesions. The abnormal cytogenetic responses of cells of people who either have AD, are destined to develop AD, or are at risk to develop AD provide the basis for the tests of the present invention.

The methods of the present invention evaluate cytogenetically DNA repair capacities which distinguish compounds or compositions of compounds which can protect against DNA fluorescent-light induced damage. Both of those processes involve the damaging of cultured cells' DNA with cool-white fluorescent light in the presence of a putative DNA protectant, followed by addition to the cultures of a chemical which blocks DNA-repair processes. The effect of the chemical is then calculated by subtracting the amount of chromatid damage observed in the absence of a chemical from that in its presence. If the compound is a DNA protectant, no differences are found using normal cells in the presence or absence of ara-C in the $G_2$-phase test or using AD cells in the presence or absence of caffeine $G_1$-phase test.

It is expected that any chemical which inhibits repair during S-phase, i.e., which inhibits post-replication repair, can act as a substitute for caffeine in the $G_1$-phase test. It is also expected that any chemical which inhibits DNA repair during $G_2$, i.e., which inhibits DNA repair synthesis and/or DNA ligation during $G_2$-phase, can act as a substitute for ara-C in the $G_2$-phase test.

"Normal cells" are defined herein as cells which, in the $G_2$-test described in Example 2 hereinbelow and also in U.S. application Ser. No. 08/611,330 (35) and Parshad et al. (1996) (36), show a significant increase in the frequency of chromatid breaks in the fluorescent light-irradiated cell cultures to which ara-C is added, as compared to the frequency of chromatid breaks in the irradiated cell cultures to which ara-C is not added.

"AD" cells are defined herein as those which, in the $G_1$-test described in Example 1 hereinbelow and also in U.S. application Ser. No. 08/611,330 (35) and Parshad et al. (1996) (36), show a significant increase in the frequency of chromatid breaks in the fluorescent light-irradiated cell cultures to which caffeine is added, as compared to the frequency of chromatid breaks in the irradiated cell cultures to which caffeine is not added.

"DNA protectant", as defined herein, is a compound, or compositions of compounds, which protects against the formation of induced lesions in the methods of the invention using the $G_1$-phase test and $G_2$-phase test and fluorescent light or x-rays. The DNA protectant, or suspected DNA protectant, is preferably an anti-oxidant and/or free-radical scavenger, since prior studies have indicated that free radicals, and especially oxygen free radicals, are agents which cause chromosomal aberrations in cells irradiated with fluorescent light in tissue culture (22, 41). The DNA protectant, or suspected DNA protectant, may be any compound or composition of compounds that inactivates free radicals or interferes with their formation, but preferably will be a compound, or composition containing a compound, which is able to enter a cell, and reach its nucleus, in order to be in close enough proximity to the cellular DNA to interfere with or quench the DNA damaging agent(s). At certain concentration ranges, increasing the concentration of a DNA protectant is expected to lower the CBF in a dose-related manner, after treatment with fluorescent light or x-rays and addition of a DNA repair inhibitor, as compared to the CBF obtained in the absence of a DNA protectant.

Theaflavin is a DNA protectant exemplified herein in Example 4. Other DNA protectants include green or black tea extracts (GTE or BTE) (25), their polyphenols (GTP or BTP) (25) or curcumin (37). The compositions and chemical structures of these compounds have been described (26, 37). These compounds have been shown by some of the inventors to significantly reduce the frequency of X-ray and fluorescent radiation-induced chromatid breaks in the $G_2$-phase test in normal human cells in culture. Curcumin at a concentration of 100 μg/ml inhibited mitosis in the presence or absence of light exposure. Increasing the concentration of curcumin from 10 to 80 μg/ml lowered the CBF after fluorescent light irradiation and the addition of ara-C in a dose-related manner. (Table 4, Example 5). However, the green tea polyphenol (GTP), (-) epigallocatechin gallata (EGCG), did not lower the frequency of chromatid breaks at the doses tested. (Table 3, Example 5).

Some of the inventors reported previously (38) that mannitol, a scavenger of the reactive free hydroxyl radical (OH), or catalase, which decomposes hydrogen peroxide when added to the culture medium during or after x-irradiation decreased chromatid break frequency in a dose-related manner. X-rays are known to generate OH through radiolysis of water (39). These observations suggest that the protection afforded by the tea components results from their action as free radical scavengers and their known antioxidant properties.

It should be noted that the methods of the present invention use fluorescent light to irradiate the cells in both the $G_1$- and $G_2$-phase tests. Ionizing radiation (e.g., x-rays) is not used in the $G_1$-phase test of the present invention because x-rays produce a mitotic block in the early $G_2$ phase, thereby perturbing the cell cycle and interfering with the test, for the cells irradiated in $G_1$ phase must subsequently progress through S-phase, the $G_2$-phase, and into mitosis in an appropriate time in order to be harvested.

In the processes of the present invention: 1) the cells are irradiated with cool-white fluorescent light or x-rays, 2) after irradiation, chemicals which inhibit DNA repair (caffeine for the $G_1$-phase test and ara-C for the $G_2$-phase test) are added to the cultures; 3) the experiments are conducted so that the metaphase cells had been in a known phase of the cell cycle at the time of irradiation (e.g., in the $G_1$-phase for the caffeine experiments and in the $G_2$-phase for the ara-C experiments) rather than in just the $G_0$ phase or in several phases (the irradiation protocols for $G_1$ and $G_2$ phase tests are based on the observation that different cell lines grown under constant conditions at 37° C. have a variable $G_1$ period but relatively constant periods of $G_2$ (2–5 h), S (6–9 h), and M (½–1 h)); 4) chromatid damage is quantified (measured as chromatid break frequencies) instead of quantifying any chromosomal aberrations (e.g., chromosome breaks, dicentrics, fragments, and interchanges).

To ensure accuracy and reproducibility of results in the present process, various process parameters merit particular consideration and control samples should always be run. The parameters include: pH, temperature, cell density, culture medium or serum, microbial contamination and visible light exposure (effective wavelength 405 nm). These are each discussed in U.S. Pat. No. 4,933,274, which is incorporated by reference herein.

The following examples are exemplary of the present processes and incorporate suitable process parameters for use herein. These parameters may be varied, however, and the following should not be deemed limiting.

MATERIALS AND METHODS

Source of Cells. Cultures of skin fibroblasts developed from biopsy material as described for example by Goetz, I. E. "Growth of human skin fibroblasts from punch biopsies". TCA Manual, 1:13–15 (1975), Tissue Culture Methods and Applications, P. F. Kruse, Jr. and M. K. Patterson, Jr. Eds., Academic Press, New York, (1973) and established cell lines obtained from cell repositories such as the American Type Culture Collection, 12301 Parklawn Drive, Rockville, Md. 20852 or NIGMS Human Genetic Mutant Cell Repository, Coriell Institute of Medical Research, 401 Haddon Avenue, Camden, N.J. 08103 may be used. For instance, in the examples described below various lines of skin fibroblasts were obtained from the NIGMS Human Genetic Mutant Cell Repository (GM) and the NIH Aging Cell Repository (AG).

Quantification of Chromatid Damage. To quantify chromatid damages in both the test and control samples, 50 to 100 metaphase cells from each culture are examined for chromatid breaks. Chromatid interchanges generally do not occur for they arise infrequently in human fibroblasts. Breaks appear as chromatid discontinuities with displacement of the broken segment. What had previously been called gaps (non-staining regions) show no displacement of the segment distal to the lesion, and are scored only if they are longer than the chromatid width (See, ISCN: An International System for Human Cytogenetic Nomenclature. Cytogenet. Cell Genet., 21:309–404 (1978). (Note that the chromatid breaks and gaps are referred to simply as chromatid breaks herein). Cells in prometaphase or metaphase cells with understained or overstained chromosomes are not considered suitable for analysis because understained chromosomes could have unstained gap-like regions, while overstaining could obscure gaps.

Statistical Calculations. In all cases, statistical comparisons of data are based on the t-test after taking a square root transformation of the aberration frequencies (Snedecor et al. Statistical Methods, pp. 208–213 Ames, IA:University Press (1980)).

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

$G_1$-Phase Test Using Fluorescent Light

The $G_1$ test was designed to detect the consequences of DNA damage left unrepaired in $G_1$. Briefly, in the $G_1$-phase test, the cells were irradiated with fluorescent light for 5 hours, 14 hours after which colcemid was added for 1 hour to arrest cells in metaphase. Thus, all metaphase cells examined had been in $G_1$ at the end of irradiation. Lesions not repaired in $G_1$ would persist into S phase. If these lesions inhibited DNA replication, they could result in discontinuities (i.e., gaps) in newly synthesized DNA observable as chromatid aberrations in the succeeding metaphase. These discontinuities are normally mended during S phase by a daughter-strand, postreplication repair process which can be blocked by caffeine. Therefore, to retain such discontinuities, half the cultures were exposed to caffeine from the end of irradiation through S and into $G_2$.

$G_1$ Test Rationale

XP complementation-group C and Cockayne syndrome cells, defective in NER of UV-induced DNA damage (1, 2, 4), have elevated CBs when irradiated with fluorescent light in $G_1$ phase and treated with caffeine throughout S phase and $G_2$ phase (16). Without fluorescent light, caffeine does not lead to increased CBs (16). Thus, the assay appears to reflect abnormal processing during the $G_1$ phase of fluorescent light-induced DNA damage.

$G_1$-Phase Test For Fibroblasts

A detailed protocol for quantifying the response of fibroblasts to $G_1$-phase irradiation is set forth below:

1. Log-phase skin fibroblasts are prepared by:
    (a) Transferring cells to T-25 flasks 11 days before assaying.
    (b) Renewing the culture medium on days 8 and 6 before assay. One medium found suitable for use is Dulbecco's Modified Eagle's medium ("DMEM"—Morton, H. C. "A survey of commercially available tissue culture media", In Vitro 6:89–108 (1970)), a chemical nutrient solution designed for growing cells in culture, with 4.5 g/l glucose and 10% fetal bovine serum (Bio Whitaker, Walkersville, Md. & ICN Biomedical, Inc., Costa Mesa, Calif., respectively).
    (c) Subculturing the fibroblasts on day 4 before assay.
    (d) Renewing the culture medium 24 hours before assay. Cultures should be subconfluent for assay.
    (e) Adding a known or suspected DNA protectant to the culture medium of at least some of the cultures (e.g., to a sufficient number of cultures to more easily obtain a statistically significant result) 1 hour prior to irradiation.
2. To prepare replicate cultures for irradiation:
    (a) Rinse culture with EDTA (ethylene diamine tetraacetic acid) (versene 1:5000, Bio Whitaker) for about 30 seconds.
    (b) Withdraw versene and add just enough trypsin-EDTA solution to cover cell monolayer. The trypsin-EDTA solution is prepared just prior to use by diluting 1:10 with the EDTA solution a frozen stock (1% Worthington 3X crystallized trypsin in 0.1% EDTA in Dulbecco's PBS without Ca++ or Mg++) resulting in a final trypsin concentration of 0.1%.
    (c) Gently tap flask to detach cells, then inactivate trypsin by adding a small aliquot of serum-supplemented culture medium. Bottles of medium and serum at the commercial source of preparation, during shipping, storage and use, as well as cultures in the medium, should at all times be protected from light of wavelength <500 nm to avoid adversely affecting the assay results. Suggested means include aluminum foil wraps, yellow bags, gold or red room lights, and appropriate light filters for microscope observation.
    (d) Adjust cell suspension to about $0.5–1 \times 10^5$ cells/2 ml medium. For reproducibility, inoculum size should be adjusted to obtain equivalent cell densities (e.g. 75% confluence) at the time of irradiation 48 hours later.
    (e) Inoculate cell suspensions into Leighton tubes, each containing a 9×50 mm coverslip (No. 1 thickness Bellco Glass Co., Vineland, N.J.). For best results, equilibrate gas phase with humidified 10% $CO_2$ in air, seal with #0 silicone stopper and incubate at 37° C. It should be noted that maintenance of physiologic pH is necessary to avoid adversely affecting test results.
    (f) Alternatively, log-phase skin fibroblasts can be inoculated into T-25 flasks at a cell density to yield a semi-confluent cell sheet after 48 h incubation.
    (g) Renew medium 24 hours before irradiation.
3. To irradiate cultures:
    (a) Expose cultures of cells from normal and presumed AD patients for 5 h to fluorescent light at 37° C. The light source can be a desk lamp fitted with a cool-white 15-W fluorescent Westinghouse bulb (F15 T8-CW). Cultures are exposed at a distance to yield an intensity of 5 W/m² at the growth surface as measured by an 1L 700 research radiometer (International Light Inc., Dexter Industrial Green, Newburyport, Mass.). Control unirradiated cultures are handled identically but shielded from light.
    (b) Add caffeine (0.25 mM, Sigma) to approximately half of the irradiated cultures; incubate for an additional 15 h completely shielded from light.
    (c) Add colcemid (0.1 ug/ml, Gibco, Grand Island, N.Y.) to all cultures during the last hour.

4. To process cells for chromosome analysis:
   (a) After about 1 hour incubation with Colcemid (N-desacetyl-N-methylcochicine) at 37° C., decant medium, invert culture and gently add to roof of culture vessel 2 to 5 ml 0.53% KCl in distilled $H_2O$ prewarmed to 37° C. Return culture to original position and incubate for 15 minutes at 37° C. Alternatively, cells can be removed with trypsin from the T-25 flasks and processed in suspension as described later for lymphocytes.
   (b) Prepare fixative at room temperature just before use. A suitable fixative comprises 1 part glacial acetic acid:3 parts absolute methanol.
   (c) Decant KCl solution, invert culture and gently add to roof of the culture vessel 2 to 5 ml fixative. Return culture to original position and fix for about 30 minutes at room temperature.
   (d) Remove coverslip from vessel, air-dry at an angle and, preferably, store for at least 24 hours before staining.
   (e) Stain coverslip about 4 minutes with aqueous Wright-Giemsa (3 parts) plus distilled water (125 parts) (Harleco, Gibbstown, N.J.). Rinse in tap water, air dry, dip in xylene and mount on a clean slide with a mounting medium.
5. To quantify chromatid aberrations:
   (a) Scan samples for complete well-spread metaphase cells.
   (b) Score each metaphase cell for number of chromatid breaks (showing distinct dislocation and misalignment of the chromatid fragment), chromatid gaps (or achromatic lesions longer than the width of the chromatid, showing apparent chromatid discontinuity, but no dislocation), and other chromosomal abnormalities as experimental objectives dictate. Note that the chromatid breaks and gaps are referred to simply as chromatid breaks herein.
6. Determine caffeine effect (see table 1).

$G_1$-Phase Test For Peripheral Blood Lymphocytes

To quantify the response of peripheral blood lymphocytes to $G_1$-phase irradiation, lymphocytes are prepared as described in steps 1–10 in Example 2 below and are tested in the $G_1$-phase test as described in steps 3–6 immediately above, except that step 8 in Example 2 below is conducted at 48 h instead of at 72 h, and in step 3(b), above, 2 mM caffeine is used instead of 0.25 mM and the cell cultures are incubated for 18 hours instead of 15 hours after the addition of caffeine and before the addition of colcemid.

EXAMPLE 2

$G_2$-Phase Test Using Fluorescent Light

The $G_2$ test, in which nucleotide excision repair is blocked by ara-C, was designed to measure directly the extent of the incision step of excision repair in normal and patient cells. In nucleotide excision repair the damaged DNA strand is enzymatically incised, after which the damaged and some neighboring nucleotides are removed. The resulting space is filled in by a DNA polymerase whose action can be inhibited by ara-C. Such inhibition results in an unligatable segment of DNA, which can then lead to a chromatid aberration in the succeeding metaphase. Briefly, in the $G_2$ test the cells were irradiated with fluorescent light for 2 to 3 hours, followed shortly by addition of colcemid to arrest cells in metaphase, so that all metaphase cells examined would have been in $G_2$ by the end of irradiation. Furthermore, ara-C was added to half the cultures just 10 min. after the end of irradiation. Thus, all these metaphase cells examined would have been exposed to ara-C during at least some portion of their $G_2$.

$G_2$ Test Rationale

NER removes bulky lesions as part of an oligonucleotide (1–4, 7), resulting in discontinuities in DNA that are filled by a DNA polymerase. The newly synthesized segments are then ligated to the remaining strand. The polymerase step is inhibited by ara-C (24), resulting in unfilled segments of DNA which lead to CBs in the subsequent metaphase.

$G_2$-Phase Test

A detailed protocol for quantifying the response of fibroblasts and peripheral blood lymphocytes to $G_2$-phase irradiation using fluorescent light is set forth below:
Skin Fibroblasts
1. Add a known or suspected DNA protectant to the culture medium of at least some of the cultures (e.g., to a sufficient number of cultures to more easily obtain a statistically significant result) 1 hour prior to irradiation.
2. To test for repair of damage inflicted during $G_2$-phase, cells grown on coverslips in Leighton tubes or in T-25 flasks are exposed for 3 h at 37° C. to cool-white fluorescent light ($8W/m^2$ at the growth surface). For light source, see $G_1$ test but use two light bulbs.
3. Add the DNA repair inhibitor, 1β-D-arabinofuranosylcytosine (ara-C, 50 μM, Sigma) to approximately half the cultures at 10 min after light exposure and colcemid (0.1 μg/ml) to all cultures at 30 min postexposure for 2 h.
4. Process for chromosome analysis as in $G_1$-phase test, step 4.
5. Determine ara-C effect (see tables 2 and 3).
Peripheral blood lymphocytes
1. Prepare RPMI 1640 medium with 15% fetal bovine serum, 10 μl/ml heparin and 0.1 mg/ml Gentamicin (Gibco).
2. Dispense 8 ml to sterile glass tubes (Wheaton Glass Co.; obtained from Arthur Thomas) with open-top screw caps supplied with a septum for needle insertion. These tubes are supplied to physicians for collecting blood samples.
3. Freshly drawn blood (2 ml) is added aseptically directly through each tube septum by syringe needle. These blood samples must be maintained at room temperature until processed within 24 h.
4. Centrifuge blood samples at 150 g for 9 min, and discard supernatant.
5. Resuspend cells in 20 ml of medium prepared in step 1 and transfer to a T-25 culture flask.
Alternatively, the blood may be collected in a sterile vacutainer tube (Beckton-Dickenson Vacutainer Systems, USA, Rutherford, N.J.) containing powdered sodium heparin. 2 ml of the blood drawn in the vacutainer may be added to 20 ml of culture medium prepared in step 1 contained in a T-25 culture flask.
6. Warm the blood culture to 37° C. and add 0.44 ml PHA (9 mg/ml HA15, Wellcome Diagnostics) also warmed to 37° C. Gas the mixture with 10% $CO_2$ in air and incubate upright at 37° C. for 72 h.
7. At approximately 24 and 48 h invert the culture flask 5–8 times to resuspend the cells. This enhances lymphocyte proliferation.
8. At 71 hr (i.e., 1 hour prior to irradiation), add a known or suspected DNA protectant to the culture medium of at least some of the cultures (e.g., to a sufficient number of cultures to more easily obtain a statistically significant result).
9. At 72 h pipette out 8 ml of the supernatant without disturbing the cells at the bottom of the flask, and save the supernatant. Thoroughly mix the remaining supernatant with the cells. Using a 9 inch glass pasteur pipette fill a Wintrobe hematocrit tube (Clay Adams, a Division of Becton Dickinson, Parsippany, N.J.) to the top line and spin at 2260 g for 10 minutes. This, as well as other procedures up to fixation, should be carried out at 37° C.

10. A reading of 0.5 on the Wintrobe tube is considered standard for a 5 ml sample. Therefore, to calculate the amount of blood culture needed, use the formula 0.5 divided by the hematocrit reading multiplied by 5.
11. For an experiment, pipette the correct amount of culture as determined above (usually less than 5 ml) into a T-25 flask and add supernatant from step 8 to yield 5 ml. Equilibrate gas phase with humidified 10% $CO_2$ in air.
12. Expose cultures to fluorescent light (8W/$m^2$ for 3 h. (For light source, see $G_2$ phase test using skin fibroblasts.)
13. Add the DNA repair inhibitor, 1β-D-arabinofuranosylcytosine (ara-C, 50 μM, Sigma) at 10 min or 30 min post exposure to approximately half of the cultures, and add colcemid (0.1 μg/ml) at 30 min post exposure for 1 h or 2 h to all the cultures. Equilibrate gas phase with humidified 10% $CO_2$ in air and stopper tubes.
14. Centrifuge cells in 15 ml borosilicate centrifuge tubes at 150 g for 9 minutes. Draw off the supernatant down to the pellet and add 10 ml freshly prepared 0.53% KCl. Mix and incubate for 9 minutes.
15. Spin again at 150 g for 9 minutes and draw off the clear, red supernatant down to approximately 0.75 ml. Mix this remaining supernatant with the pellet.
16. Immediately fix in cold glacial acetic acid-methanol (1:3) (kept on ice at 4° C.) adding only a few drops at first with continuous mixing. Use only a glass pipette and avoid vigorous pipetting. After the cells and hemoglobin are well dispersed add more fixative up to a final amount of 6–8 ml.
17. Store in an ice bath (4° C.) for 30 min. Spin at 150 g for 9 minutes and remove supernatant. Add a drop or two of fresh fixative, resuspend pellet and bring up to 5 ml. Store in refrigerator at least overnight for better metaphase spreads.
18. To make the metaphase spreads, spin the tubes, withdraw the fixative and resuspend in 2 ml fresh fixative. Spin again, remove fixative and resuspend in 8–24 drops (depending on size of pellet) fresh fixative. Drop onto slides in a humid atmosphere and dry overnight at room temperature.
19. Stain slides for 4 minutes in aqueous Wright-Giemsa (3 parts) plus distilled water (125 parts). Rinse in tap water, air-dry overnight at room temperature.
20. Mount with Permount and dry at room temperature.
21. Determine ara-C effect (see table 4).

$G_2$-Phase Test Using X-Rays

A detailed protocol for quantifying the response of fibroblasts and peripheral blood lymphocytes to $G_2$-phase irradiation using x-rays is set forth in U.S. Pat. No. 5,933,274 (incorporated herein by reference).

EXAMPLE 3

$G_2$ Test with Lymphocytes Exposed to 254-nm UV

For this test, Petridish covers were removed, cell suspensions were irradiated with 12 J/$m^2$ 254-nm UV (General Electric germicidal lamp G15T8; incident flux, 2 J/$m^2$/sec), 9 ml of culture medium was added, and cells were transferred to 15-ml centrifuge tubes. Thirty minutes later ara-C (final concentration, 12 μg/ml) and colcemid (final concentration, 0.5 μg/ml) were added for 1 h when cells were processed for metaphase analysis as described (23).

UV alone did not induce significant numbers of CBs in the normal, AD, or XP complementation-group A (XP-A) cells (Table 1). When ara-C was added following irradiation, normal and AD, but not XP-A, cells showed marked ara-C effects.

TABLE 1

$G_2$-test with 254-nm UV-irradiated lymphocytes

| Donor | | | | CBF | | ara-C effect |
|---|---|---|---|---|---|---|
| Type | No. | Age, yr | Sex | UV alone | UV followed by ara-C | |
| Normal | 31 | 32 | F | 0 | 46 | 46 |
| Spor AD | 9 | 75 | F | 0 | 38 | 38 |
| XP-A | 3 | 23 | M | 2 | 2 | 0 |

CBF, number of CBs per 100 metaphase cells, ara-C effect, CBF for "UV followed by ara-C" less that for "UV alone." Spor, sporadic, XP-A donor 3, patient XP19BE. With ara-C, unirradiated cells of all three donors had CBFs of ≦4.

EXAMPLE 4

Effect of Free-Radical Scavenger TFM with 254-nm UV or FL

A filter-sterilized aqueous solution of theaflavin mixture (TFM) (lot LN0046-01; Thomas J. Lipton Co., Englewood, N.J.), comprised of polyphenol antioxidants extracted from black tea (25, 26), was added to lymphocyte cultures (final concentration 100 μg/ml) 1 h before irradiation with UV or fluorescent light.

With UV-irradiated cells, TFM did not change the ara-C effect of normal or AD cells (Table 2). With fluorescent light-irradiated cells, TFM prevented the ara-C effect of normal cells in the $G_2$-phase test and the caffeine effect of AD cells in the $G_1$ phase test (Table 2).

TABLE 2

Exposure of normal and AD lymphocytes to 254-nm UV or to FL in the presence of free radical scavenger TFM

| Donor | | | CBF | ara-C/caffeine* effect† with TFM |
|---|---|---|---|---|
| Type | No | UV/FL and TFM | UV/FL and TFM followed by ara-C/caffeine* | |
| $G_2$ test, UV | | | | |
| Normal | 31 | 0 | 44 | 44 |
| Spor AD | 9 | 0 | 34 | 34 |
| $G_2$ test, FL | | | | |
| Normal | 30 | 2 | 2 | 0‡ |
| Normal | 31 | 2 | 2 | 0‡ |
| $G_1$ test, FL | | | | |
| Spor AD | 9 | 4 | 8§ | 4 |

For CBF, see Table 1; Spor, sporadic.
*ara-C for $G_2$ test; caffeine for $G_1$ test.
†ara-C/caffeine effect = CBF for "UV/FL and TFM followed by ara-C/caffeine" less that for "UV/FL and TFM."
‡Without TFM, normal donors 30 and 31 had ara-C effects with FL of 48 and 26, respectively.
§Without TFM, this CBF was 82.

EXAMPLE 5

Normal human cells proficiently repair the light-induced DNA damage that leads to chromatid breaks. Therefore, to determine the extent of light-induced damage in the presence or absence of tea extracts and polyphenols in the $G_2$-phase test, repair was inhibited by adding ara-C to the culture medium 0.5 to 1.5 h after light exposure. Under these conditions, fluorescent light produced a CBF of 34 in skin fibroblasts of the normal cell line, GM5757 (Table 3). Addition of GTP or BTP to the culture medium 1 h before light exposure reduced the CBF to 19 and 9 respectively. This reduction was statistically significant ($p<10^{-3}$ and $p<10^{-5}$ for GTP and BTP respectively). EGCG, on the other hand, had no effect on CBF.

Table 3 further shows the effects of BTE, GTE, and their primary polyphenols, TFM and EGCG respectively, on PHA-stimulated peripheral blood lymphocytes from three different normal donors. Light exposure with or without added tea extracts or their polyphenols yielded a low CBF of $\leq 2$. This CBF was increased to 28 to 32 when ara-C was added after light exposure. Addition of BTE, GTE or TFM reduced this CBF to 2, 0 and 2 respectively. EGCG on the other hand had no effect.

Table 4 shows the effect of curcumin on fluorescent light-induced chromatid breaks in PHA-stimulated peripheral blood lymphocytes from two donors. Light exposure produced no chromatid breaks in cells of donor No. 1. Addition of ara-C increased the CBF to 84 and 60 in cells of donors Nos. 1 and 2 respectively. Curcumin at a concentration of 100 μg/ml inhibited mitosis in the presence or absence of light exposure. Increasing the concentration of curcumin from 10 to 80 μg/ml lowered the CBF in a dose-related manner.

TABLE 3

Effect of Black Tea Extract (BTE), Black Tea Polyphenols (BTP), Green Tea Extract (GTE), Green Tea Polyphenols (GTP), Theaflavin Mixture (TFM) and (-) Epigallocatechin gallate (EGCG) on Fluorescent Light (FL)-induced Chromatid Breaks in Human Cells in the presence or absence of ara-C in PHA-stimulated blood lymphocytes from normal donors.

| | Chromatid Breaks/100 Metaphase Cells | | | |
| | Skin Fibroblasts | Blood Lymphocytes | | |
| Treatment | GM 5757 | Donor #1 | Donor #2 | Donor #3 |
|---|---|---|---|---|
| FL alone | 3 | 2 | 2 | 0 |
| FL + BTE | — | 2 | — | — |
| FL + GTE | — | 0 | — | — |
| FL + TFM | — | — | 2 | 2 |
| FL + EGCG | — | — | 2 | 2 |
| FL + araC | 34 | 32 | 28 | 32 |
| FL + araC + BTP | 8.8 | — | — | — |
| FL + araC + BTE | — | 2 | — | — |
| FL + araC + GTP | 18.6 | — | — | — |
| FL + araC + GTE | — | 0 | — | — |
| FL + araC + TFM | — | — | 2 | 2 |
| FL + araC + EGCG | 43 | — | 30 | 34 |

TABLE 4

Effect of curcumin (Cu) on fluorescent light (FL)-induced chromatid breaks in the presence of ara-C in PHA-stimulated blood lymphocytes from normal donor Nos. 1 and 2.

| | Chromatid Breaks/100 Metaphase Cells | |
| Treatment | Donor #1 | Donor #2 |
|---|---|---|
| FL + araC | 84 | 60 |
| FL + araC + Cu (10 μg/ml) | 88 | — |
| FL + araC + Cu (20 μg/ml) | 68 | — |
| FL + araC + Cu (40 μg/ml) | 34 | 32 |
| FL + araC + Cu (60 μg/ml) | — | 18 |
| FL + araC + Cu (80 μg/ml) | — | 8 |

In these experiments, extracts of black and green tea and their respective polyphenols, including theaflavin mixture and (-) epigallocatechin gallate, as well as curcumin from tumeric, were supplied by Dr. D. A. Balentine of the Thomas J. Lipton Company, Englewood Cliffs, N.J. The tea compounds were dissolved in 4X glass-distilled water and filter sterilized. Curcumin was supplied as a 1% solution in a 50:50 mixture of polyethyleneglycol and glycerine.

EXAMPLE 6

Forty-eight hour cultures of skin fibroblasts grown on 9×50 mm coverslips in Leighton tubes were x-irradiated (53 rads) as described (42). The culture medium was renewed immediately after x-irradiation and cells arrested in metaphase with colcemid (0.1 μg/ml) from 0 to 0.5 hours post irradiation. In certain cultures the tea components were added to the culture medium 1 hour before x-irradiation and again added to the medium at its renewal after irradiation. The final concentrations of the tea components were 100 μg/ml, unless otherwise indicated.

Table 5 shows the effects of GTP, BTP and EGCG on x-ray induced chromatid breaks in two lines of human skin fibroblasts. X-irradiation (53 rads) produced chromatid breaks (CBFs) of 80 and 56 in cells of lines GM 5565 and 5757, respectively. Addition of GTP or BTP to the culture medium 1 hour before x-irradiation significantly reduced these CBFs. EGCG, on the other hand, did not affect the x-ray induced CBFs in either cell line. GTP or BTP might produce a mitotic block resulting in an accumulation of metaphase cells during the hour prior to x-irradiation. Metaphase cells do not show radiation-induced chromatid breaks (unpublished observations), and thus could give the false impression of having been protected by GTP or BTP. We therefore determined the number of cells entering metaphase in cultures irradiated or not irradiated in the presence of GTP or EGCG. The ratios of irradiated to nonirradiated were equivalent after treatment with GTP or EGCG, i.e., 96.5 and 93.3, respectively. These data show that reduction of CBF in the presence of the tea polyphenols GTP and BTP does not result from a mitotic block. The reduction thus appears to result from their radioprotective actions.

TABLE 5

Effect of Green Tea Polyphenols (GTP), Black Tea
Polyphenols (BTP), and (-) Epigallocatechin gallate (EGCG)
on X-ray (53 rads)-induced Chromatid Breaks in Human
Fibroblast Cell Lines.

| | Chromatid Breaks/100 Metaphase Cells | |
|---|---|---|
| Treatment | Line GM 5565 | Line GM 5757 |
| None | 1.5 | 2 |
| X-ray alone | 80 | 56 |
| X-ray + GTP | 12.9* | 9.8** |
| X-ray + BTP | 16.7*** | 10.4*** |
| X-ray + EGCG | 93.6 | 56.9 |

*$p < 10^{-3}$
**$p < 10^{-4}$
***$p < 10^{-5}$

These results show that the addition of green or black tea extracts, their respective polyphenols, or theaflavin mixture significantly reduce the frequencies of x-ray induced chromatid breaks in human skin fibroblasts. No reduction was, however, seen with EGCG at the doses tested.

DISCUSSION

Evidence that the tests of the invention are reflecting DNA repair include the results of the $G_2$ test using 254-nm UV in which AD cells, which are proficient in repairing UV-induced DNA damage (8, 10–12), have a normal ara-C effect (Table 1), whereas XP-A cells, which are defective in NER of such damage (1–6, 9), show no ara-C effect. Thus, the ara-C effect of UV-irradiated normal and AD cells may be reflecting NER of bulky lesions known to be induced directly by UV without the intervention of free radicals (1). As expected, the presence of the free-radical scavenger TFM (25, 26) during irradiation has no effect on this UV-induced ara-C effect (Table 1 versus Table 2).

In contrast to 254-nm UV, FL causes most of its DNA base damage in cells in tissue culture indirectly via the generation of free radicals (22). Such radicals appear to be producing the FL-induced CBs in our tests because CBs were prevented when TFM was present during irradiation (Table 2). Some free radical-induced DNA lesions are bulky (1,7), require NER (7), and, therefore, are not repaired by XP-A cells (7). Other lesions are nonbulky, subject initially to base excision repair (1, 2, 7, 28, 29), and repaired normally by XP-A cells (7, 28, 29), as has been demonstrated with particular reference to 8-hydroxyguanine (29) and thymine glycols (28), the two most common types of these free radical-induced base lesions. Since NER-deficient, base excision repair-proficient XP-A cells showed no ara-C effect after irradiation with FL, we believe the ara-C effect of FL-irradiated normal cells reflects NER and not base excision repair. While the substrate specificity of the NER system is spectral and includes a wide variety of bulky adducts, the chemistries of which are all significantly different (30), mutations can inactive repair of one but not another bulky lesion. Thus, we hypothesize that AD cells, with normal NER of UV-induced thymine dimers, have defective NER of a free radical-induced bulky lesion. If so, the situation is similar to that in the following cells with known defects in NER of one, but not another, UV-induced bulky lesion, although all such lesions are normally repaired by NER: Cockayne syndrome (31), XP-A revertant (32), XP complementation-group D (31), and trichothiodystrophy (31) cells.

AD has features similar to those of diseases with NER defects: no increase in cancer, as in Cockayne syndrome (1, 2, 4) and trichothiodystrophy (1, 2, 31); adult onset of neurodegeneration, as in some XP complementation-group C patients (5, 6); and degeneration of certain neuron groups but not others, as in XP-A patients (5, 6). If death of nerve cells in AD results from failure to repair free radical-induced DNA damage, antioxidant therapy may prevent or delay neurodegeneration.

We found normal survival of FL-irradiated AD cells (data not shown). Normal survival with an unrepaired lesion occurs with UV-irradiated XP-A revertant (32) and XP complementation-group E cells (33). X-rayed XP-A cells have normal survival (9), even though they are unable to repair a class of free radical-induced base lesions generated by ionizing radiation (7). To explain this apparent paradox, it was suggested (7) that since free radicals generate several different classes of DNA lesions in addition to chain breaks, defective repair of only one type of such damage in XP-A cells may be difficult to detect in cytotoxicity assays.

General Comments

The fact that there are defects in DNA repair in many different diseases, such as the various types of cancers, does not mean that the defects are due to the same mechanism or gene nor does it mean that the DNA repair defects of cells from individuals with these other diseases would give the same results in the $G_1$- and $G_2$-phase tests as cells from individuals who either have AD or who are destined to develop AD. In fact, this is statistically unlikely. If the basis of the distinction between normal and AD cells was another genetic defect not associated with AD, then one would expect that some of the normals would have this defect and that some of the AD and DS individuals would not have this defect and that there would not be a statistically significant difference in the $G_1$- and $G_2$-phase tests of the present invention between cells from normal individuals as compared to cells from those who either have AD or are destined to develop AD. Instead, there is a statistically significant difference (P<0.05) between cells from normal individuals as compared to cells from those who either have AD or are destined to develop AD in the $G_1$- and $G_2$-phase tests of the present invention.

Furthermore, cells from individuals with different diseases with defects in DNA repair, such as cells from individuals with various cancers, behave differently from AD cells when used in the $G_2$-phase test assay of the prior art. For example, cells from individuals with cancer have a marked increase in total chromatid breaks as compared to normal cells when irradiated with either X-rays or fluorescent light in $G_2$-phase without the addition of a DNA repair inhibitor such as ara-C (see, Sanford et al., U.S. Pat. No. 4,933,274, col. 1, lines 37–49), whereas cells from individuals with AD behave like normal cells when subjected to the same conditions. Rather, cells from individuals with AD differ from those of normal individuals only when ara-C is added, as taught in U.S. application Ser. No. 08/611,330 (35) and also in Parshad et al. (1996) (36). Therefore, the effect of X-ray or fluorescent light irradiation in $G_2$-phase is quite different on cells from individuals with cancer as compared to cells from individuals with AD. Thus, the mechanism and/or gene responsible for DNA repair defects in cells from individuals with cancer is different from that in cells from individuals with AD and, in any event, cells from individuals with cancer and/or genetically predisposed to cancer can be distinguished from cells from individuals with AD.

Precautions and Comments

To ensure accuracy and reproducibility of results in the present process:
1. Cultures must at all times be free of bacteria.
2. The temperature of cultures must be maintained at 37° C. up until time of fixation. A walk-in incubator room for 37° C. is recommended.
3. The pH of cultures must be maintained at physiological level (~7.2).
4. The serum lots should be pre-screened to ensure adequate DNA repair.
5. Coding of the samples should be done at each stage of the process to reduce the chance of investigator bias. For example, the person obtaining the cell cultures or blood samples should code them for the person performing the irradiating and subsequent steps and the latter person should re-code them for the person counting the chromatid breaks and gaps. However, caution must be taken to keep accurate records to avoid mixing up the samples. Note that the chromatid breaks and gaps are referred to simply as chromatid breaks herein.
6. When conducting experiments using fibroblast cell lines, it is preferable to work from an early expansion of a cell line since the possibility exists that the use of later expansions may be problematic.
7. When conducting experiments using peripheral blood, it is preferable to use blood collected within a few hours of conducting the experiment, since it is possible that longer times between the time of collection and time of conducting the experiment may have adverse effects. It is also preferable that the patient from whom the blood is collected not be on any medication, especially medication which may interfere with the generation of and/or half-life of free radicals. Collection time and medication are not expected to be problems when lymphoblastoid or culture cell lines are used.

REFERENCES

1. Friedberg, E. C., Walker, G. C. & Siede,W. (1995) *DNA Repair and Mutagenesis* (Am. Soc. for Microbiol., Washington, DC).
2. Hanawalt, P. C. (1994) *Science* 266, 1957–1958.
3. Grossman, L. & Thiagalingam, S. (1993) *J. Biol. Chem.* 268, 16871–16874.
4. Bundey, S. (1992) *Genetics and Neurology* (Churchill Livingston, Edinburgh, U.K.)
5. Robbins, J. H. (1989) *J. Child Neurol.* 4, 143–146.
6. Robbins, J. H. Brumback, R. A., Mendiones, M., Barrett, S. F., Carl, J. R., Cho, S., Denckla, M. B., Ganges, M. B., Gerber, L. H., Guthrie, R. A., Meer, J., Moshell, A. N., Polinsky, R. J., Ravin, P. D., Sonies, B. C. & Tarone, R. E. (1991) *Brain* 114, 1335–1361.
7. Satoh, M. S., Jones, C. J., Wood, R. D. & Lindahl, T. (1993) *Proc. Natl. Acad. Sci. USA* 90, 6335–6339.
8. Robbins, J. H., Otsuka, F., Tarone, R. E., Polinsky, R. J., Brumback, R. A. & Nee, L. E. (1985) *J. Neurol. Neurosurg. Psychiatry* 48, 916–923.
9. Otsuka, F., Tarone, R. E., Seguin, L. R. & Robbins, J. H. (1985) *J. Neurol. Sci.* 69, 103–112.
10. Robison, S. H., Munzer, J. S., Tandam, R. & Bradley, W. G. (1987) *Ann. Neurol.* 21, 250–258.
11. Link, C. J., Jr., Robbins, J. H. & Bohr, V. A. (1995) *Mutat. Res.* 336, 115–121.
12. Boerrigter, M. E. T. I., Wei, J. Y. & Vijg, J. (1992) *J. Gerontol.* 47, B177–B184.
13. Chen, P., Kidson, C. & Lavin, M. (1991) *Mutat. Res.* 256, 21–27.
14. Tobi, S. E., Moquet, J. E., Edwards, A. A., Lloyd, D. C. & Itzhaki, R. F. (1990) *J. Med. Genet.* 27, 437–440.
15. Sanford, K. K., Parshad, R., Price, F. M., Tarone, R. E. & Schapiro, M. B. (1993) *Cancer Genet. Cytogenet.* 70, 25–30.
16. Price, F. M., Parshad, R., Tarone, R. E. & Sanford, K. K. (1991) *Cancer Genet. Cytogenet.* 57, 1–10.
17. Parshad, R., Tarone, R. E. Price, F. M. & Sanford, K. K. (1993) *Mutat. Res.* 294, 149–155.
18. Baserga, R. (1985) *The Biology of Cell Reproduction* (Harvard Univ. Press, Cambridge, Mass.), pp. 17–21.
19. Sherrington, R., Rogaev, E. I., Liang, Y., Rogaeva, E. A., Levesque, G., et al. (1995) *Nature* (London) 375, 754–760.
20. McKhann, G., Drachman, D., Folstein, M., Katzman, R., Price, D. & Stadlan, E. M. (1984) *Neurology* 34, 939–944.
21. Sanford, K. K., Parshad, R., Gantt, R., Tarone, R. E., Jones, G. M. & Price, F. M. (1989) *Int. J. Radiat. Biol.* 55, 963–981.
22. Sanford, K. K., Parshad, R. & Gantt, R. (1986) in *Free Radicals, Aging and Degenerative Diseases,* eds. Johnson, J. R., Jr., Walford, R., Harman, D. & Miguel, J. (Liss, N.Y.), pp. 373–394.
23. Sanford, K. K., Parshad, R., Price, F. M., Jones, G. M., Tarone, R. E., Eierman, L., Hale, P. & Waldmann, T. A. (1990) *J. Natl. Cancer Inst.* 82, 1050–1054.
24. Fram, R. J. & Kufe, D. W. (1985) *Pharmacol Ther.* 31, 165–176.
25. Hara, Y. (1994) in *Food Phytochemicals for Cancer Prevention,* ACS Symposium Series 547, eds. Ho, C.-T., Osawa, T., Huang, M.-T. & Rosen, R. T. (Am. Chem. Soc., Washington, DC), Vol. 2, pp. 34–50.
26. Weisburger, J. H. (1995) in *Handbook of Antioxidants,* eds. Cadenas, E. & Packer, L. (Dekker, N.Y.), pp. 469–485.
27. Parshad, R., Sanford, K. K. & Jones, G. M. (1985) *Mutant. Res.* 151, 57–63.
28. Leadon, S. A. & Cooper, P. K. (1993) *Proc. Natl. Acad. Sci. USA* 90, 10499–10503.
29. Runger, T. M., Epe, B. & Moller K. (1995) *J. Invest. Dermatol.* 104, 68–73.
30. Athas, W. F., Hedayati, M. A., Matanoski, G. M., Farmer, E. R. & Grossman, L. (1991) *Cancer Res.* 51, 5786–5793.
31. Eveno, E., Bourre, F., Quilliet, X., Chevallier-Lagente, O., Roza, L., Eker, A. P. M., Kleijer, W. J., Nikaido, O., Stefanini, M., Hoeijmakers, J. H. J., Bootsma, D., Cleaver, J. E., Sarasin, A. & Mezzina, M. (1995) *Cancer Res.* 55, 4325–4332.
32. Cleaver, J. E., McDowell, M., Jones, C., Wood, R. & Karentz, D. (1994) *Somat. Cell Mol. Genet.* 20, 327–337.
33. Moshell, A. N., Tarone, R. E., Newfield, S. A., Andrews, A. D. & Robbins, J. H. (1981) *In Vitro,* 17, 299–307.
34. Wei, Q., Matanoski, G. M., Farmer, E. R., Hedayati, M. A. & Grossman, L. (1993) *Proc. Natl. Acad. Sci. USA* 90, 1614–1618.
35. U.S. application Ser. No. 08/611,330, filed Mar. 8, 1996 (and its related applications).
36. Parshad, R., Sanford, K. K., Price, F. M., Melnick, L. K., Nee, L. E., Schapiro, M. B. Tarone, R. E. and Robbins, J. H. (May 1996) "Fluorescent light-induced chromatid breaks distinguish Alzheimer disease cells from normal cells in tissue culture", *Proc. Natl. Acad. Sci., USA* 93, 5146–5150.

37. Schaich, K. M., Fisher, C., and King, R. (1994) "Formation and reactivity of free radicals in curcuminoids in *Food Phytochemicals for Cancer Prevention*, ACS Symposium Series 547, eds. Ho, C.-T., Osawa, T., Huang, M.-T. & Rosen, R. T. (Am. Chem. Soc., Washington, DC), Vol. 2, pp. 204–221.

38. Parshad, R., Gantt, R., Sanford, K. K., Jones, G. M. and Tarone, R. E., (1982) "Repair of chromosome damages induced by x-irradiation during $G_2$ phase in a line of normal human fibroblasts and its malignant derivative," *J. Natl. Cancer Inst.* 69:409–414.

39. John, H. E., Cunningham, J. R., *The Physics of Radiology,* Thomas, Springfield, Ill. (1969), pp. 680–686.

40. Steele, V. E., Sharma, S., Boone, C. W., Mehta, R., Zhu, S., Balentine, D. A. and Kelloff, G. J. "Chemopreventive efficacy of black and green tea extracts in vitro assays," *Proc. Am. Assoc. Cancer Res.* (1996), 37:273.

41. Parshad, R., Taylor, W. G., Sanford, K. K., Camalier, R. F., Gantt, R. & Tarone, R. E., "Fluorescent light induced damage in human IMR- 90 fibroblasts. Role of hydrogen peroxide and related free radicals," *Mutation Research* (1980), 73:115–124.

42. Sanford, K. K., Parshad, R., Gantt, R., Tarone, R. E., Jones, G. M. and Price, F. M. "Factors affecting and significance of $G_2$ chromatin radiosensitivity in predisposition to cancer. *Int. J. Radiat. Biol.* (1989), 55:963–981.

Modifications of the above described modes for carrying out the invention that are obvious to those of skill in the fields of immunology, protein chemistry, microbiology, medicine, and related fields are intended to be within the scope of the following claims.

Every reference cited hereinbefore is hereby incorporated by reference in its entirety.

We claim:

1. A process for identifying compounds which protect against the formation of fluorescent light-induced DNA lesions comprising the steps of:
    a) obtaining Alzheimer disease cells;
    b) culturing the cells to obtain cell cultures wherein $G_1$-phase cells are present;
    c) adding a compound to the cell cultures prior to irradiating the cell cultures with fluorescent light, which compound is suspected of protecting against the formation of fluorescent light-induced DNA lesions;
    d) irradiating with fluorescent light the cell cultures wherein $G_1$-phase cells are present to obtain irradiated cell cultures;
    e) adding caffeine to approximately half of the irradiated cell cultures;
    f) incubating the irradiated cell cultures to allow for DNA repair;
    g) arresting cell division in the irradiated cell cultures;
    h) determining the number of chromatid breaks per 100 cells to determine the frequency of chromatid breaks in the irradiated cell cultures to which caffeine was added;
    i) determining the number of chromatid breaks per 100 cells to determine the frequency of chromatid breaks in the irradiated cell cultures to which caffeine was not added;
    j) subtracting from the frequency of chromatid breaks present in the irradiated cell cultures to which caffeine was added, the frequency of chromatid breaks present in the irradiated cell cultures to which caffeine was not added; and
    k) determining whether there is an absence of a significant increase in the frequency of chromatid breaks present in the irradiated cell cultures to which caffeine was added as compared to the frequency of chromatid breaks present in the irradiated cell cultures to which caffeine was not added;

wherein the absence of a significant increase indicates that the compound which is suspected of protecting against the formation of fluorescent light-induced DNA lesions does protect against the formation of fluorescent-light induced DNA lesions.

2. The process of claim 1 wherein cell division is arrested in the cell cultures 14 to 15 hours after caffeine is added.

3. The process of claim 1 wherein the cell cultures comprise skin fibroblasts.

4. The process of claim 3 wherein 0.25 mM caffeine is added.

5. The process of claim 1 wherein the cell cultures comprise peripheral blood lymphocytes.

6. The process of claim 5 wherein 2.0 mM caffeine is added.

7. The process of claim 6, wherein cell division is arrested in the irradiated cell cultures 18 hours after caffeine is added.

8. A process for identifying compounds which protect against the formation of fluorescent light-induced DNA lesions comprising the steps of:
    a) obtaining normal cells;
    b) culturing the cells to obtain cell cultures wherein $G_2$-phase cells are present;
    c) adding a compound to the cell cultures prior to irradiating the cell cultures with fluorescent light, which compound is suspected of protecting against the formation of fluorescent light-induced DNA lesions;
    d) irradiating with fluorescent light the cell cultures wherein $G_2$-phase cells are present to obtain irradiated cell cultures;
    e) adding ara-C to approximately half of the irradiated cell cultures;
    f) incubating the irradiated cell cultures to allow for DNA repair;
    g) arresting cell division in the irradiated cell cultures;
    h) determining the number of chromatid breaks per 100 cells to determine the frequency of chromatid breaks in the irradiated cell cultures to which ara-C was added;
    i) determining the number of chromatid breaks per 100 cells to determine the frequency of chromatid breaks in the irradiated cell cultures to which ara-C was not added;
    j) subtracting from the frequency of chromatid breaks present in the irradiated cell cultures to which ara-C was added, the frequency of chromatid breaks present in the irradiated cell cultures to which ara-C was not added; and
    k) determining whether there is an absence of a significant increase in the frequency of chromatid breaks present in the irradiated cell cultures to which ara-C was added as compared to the frequency of chromatid breaks present in the irradiated cell cultures to which ara-C was not added;

wherein the absence of a significant increase indicates that the compound which is suspected of protecting against the formation of fluorescent light-induced DNA lesions does protect against the formation of fluorescent-light induced DNA lesions.

9. The process of claim 8 wherein ara-C is added 10 min to 30 min after the cell cultures are irradiated.

10. The process of claim 8 wherein cell division is arrested 0.5 to 1.5 hours after the cells are irradiated.

11. The process of claim 8 wherein the cell cultures comprise skin fibroblasts or peripheral blood lymphocytes.

12. The process of claim 11 wherein 50 $\mu$M ara-C is added.

13. A process for identifying compounds which protect against the formation of fluorescent light-induced DNA lesions comprising the steps of:
   a) obtaining Alzheimer disease cells;
   b) culturing the cells to obtain cell cultures wherein $G_1$-phase cells are present;
   c) adding a compound to at least some of the cell cultures prior to irradiating the cell cultures with fluorescent light, which compound is suspected of protecting against the formation of fluorescent light-induced DNA lesions;
   d) irradiating with fluorescent light the cell cultures wherein $G_1$-phase cells are present to obtain irradiated cell cultures;
   e) adding caffeine to the irradiated cell cultures;
   f) incubating the irradiated cell cultures to allow for DNA repair;
   g) arresting cell division in the irradiated cell cultures;
   h) determining the number of chromatid breaks per 100 cells to determine the frequency of chromatid breaks in the irradiated cell cultures to which the compound which is suspected of protecting against the formation of fluorescent light-induced DNA lesions was added;
   i) determining the number of chromatid breaks per 100 cells to determine the frequency of chromatid breaks in the irradiated cell cultures to which the compound which is suspected of protecting against the formation of fluorescent light-induced DNA lesions was not added;
   j) determining whether there is a significant decrease in the frequency of chromatid breaks present in the irradiated cell cultures to which the compound which is suspected of protecting against the formation of fluorescent light-induced DNA lesions was added as compared to the frequency of chromatid breaks present in the irradiated cell cultures to which the compound which is suspected of protecting against the formation of fluorescent light-induced DNA lesions was not added; wherein a significant decrease indicates that the compound which is suspected of protecting against the formation of fluorescent light-induced DNA lesions does protect against the formation of fluorescent-light induced DNA lesions.

14. The process of claim 13 wherein cell division is arrested in the cell cultures 14 to 15 hours after caffeine is added.

15. The process of claim 13 wherein the cell cultures comprise skin fibroblasts.

16. The process of claim 15 wherein 0.25 mM caffeine is added.

17. The process of claim 13 wherein the cell cultures comprise peripheral blood lymphocytes.

18. The process of claim 17 wherein 2.0 mM caffeine is added.

19. The process of claim 18 wherein cell division is arrested in the irradiated cell cultures 18 hours after caffeine is added.

20. A process for identifying compounds which protect against the formation of fluorescent light-induced DNA lesions comprising the steps of:
   a) obtaining normal cells;
   b) culturing the cells to obtain cell cultures wherein $G_2$-phase cells are present;
   c) adding a compound to at least some of the cell cultures prior to irradiating the cell cultures with fluorescent light, which compound is suspected of protecting against the formation of fluorescent light-induced DNA lesions;
   d) irradiating with fluorescent light the cell cultures wherein $G_2$-phase cells are present to obtain irradiated cell cultures;
   e) adding ara-C to the irradiated cell cultures;
   f) incubating the irradiated cell cultures to allow for DNA repair;
   g) arresting cell division in the irradiated cell cultures;
   h) determining the number of chromatid breaks per 100 cells to determine the frequency of chromatid breaks in the irradiated cell cultures to which the compound suspected of protecting against the formation of fluorescent light-induced DNA lesions was added;
   i) determining the number of chromatid breaks per 100 cells to determine the frequency of chromatid breaks in the irradiated cell cultures to which the compound suspected of protecting against the formation of fluorescent light-induced DNA lesions was not added;
   j) determining whether there is a significant decrease in the frequency of chromatid breaks present in the irradiated cell cultures to which the compound suspected of protecting against the formation of fluorescent light-induced DNA lesions was added, as compared to the frequency of chromatid breaks present in the irradiated cell cultures to which the compound suspected of protecting against the formation of fluorescent light-induced DNA lesions was not added;
wherein a significant decrease indicates that the compound which is suspected of protecting against the formation of fluorescent light-induced DNA lesions does protect against the formation of fluorescent-light induced DNA lesions.

21. The process of claim 20 wherein ara-C is added 10 min to 30 min after the cell cultures are irradiated.

22. The process of claim 20 wherein cell division is arrested 0.5 to 1.5 hours after the cells are irradiated.

23. The process of claim 20 wherein the cell cultures comprise skin fibroblasts or peripheral blood lymphocytes.

24. The process of claim 23 wherein 50 $\mu$M ara-C is added.

25. A process for identifying compounds which protect against the formation of x-ray-induced DNA lesions comprising the steps of:
   a) obtaining normal cells;
   b) culturing the cells to obtain cell cultures wherein $G_2$-phase cells are present;
   c) adding a compound to the cell cultures prior to irradiating the cell cultures with x-rays, which compound is suspected of protecting against the formation of x-ray-induced DNA lesions;
   d) irradiating with x-rays the cell cultures wherein $G_2$-phase cells are present to obtain irradiated cell cultures;
   e) adding ara-C to approximately half of the irradiated cell cultures;

f) incubating the irradiated cell cultures to allow for DNA repair;

g) arresting cell division in the irradiated cell cultures;

h) determining the number of chromatid breaks per 100 cells to determine the frequency of chromatid breaks in the irradiated cell cultures to which ara-C was added;

i) determining the number of chromatid breaks per 100 cells to determine the frequency of chromatid breaks in the irradiated cell cultures to which ara-C was not added;

j) subtracting from the frequency of chromatid breaks present in the irradiated cell cultures to which ara-C was added, the frequency of chromatid breaks present in the irradiated cell cultures to which ara-C was not added; and k) determining whether there is an absence of a significant increase in the frequency of chromatid breaks present in the irradiated cell cultures to which ara-C was added as compared to the frequency of chromatid breaks present in the irradiated cell cultures to which ara-C was not added;

wherein the absence of a significant increase indicates that the compound which is suspected of protecting against the formation of x-ray-induced DNA lesions does protect against the formation of x-ray-induced DNA lesions.

26. The process of claim 25 wherein ara-C is added 10 min to 30 min after the cell cultures are irradiated.

27. The process of claim 25 wherein cell division is arrested 0.5 to 1.5 hours after the cells are irradiated.

28. The process of claim 25 wherein the cell cultures comprise skin fibroblasts or peripheral blood lymphocytes.

29. The process of claim 28 wherein 50 $\mu$M ara-C is added.

30. A process for identifying compounds which protect against the formation of x-ray-induced DNA lesions comprising the steps of:

a) obtaining normal cells;

b) culturing the cells to obtain cell cultures wherein $G_2$-phase cells are present;

c) adding a compound to at least some of the cell cultures prior to irradiating the cell cultures with x-rays, which compound is suspected of protecting against the formation of x-ray-induced DNA lesions;

d) irradiating with x-rays the cell cultures wherein $G_2$-phase cells are present to obtain irradiated cell cultures;

e) adding ara-C to the irradiated cell cultures;

f) incubating the irradiated cell cultures to allow for DNA repair;

g) arresting cell division in the irradiated cell cultures;

h) determining the number of chromatid breaks per 100 cells to determine the frequency of chromatid breaks in the irradiated cell cultures to which the compound suspected protecting against the formation of x-ray-induced DNA lesions was added;

i) determining the number of chromatid breaks per 100 cells to determine the frequency of chromatid breaks in the irradiated cell cultures to which the compound suspected of protecting against the formation of x-ray-induced DNA lesions was not added;

j) determining whether there is a significant decrease in the frequency of chromatid breaks present in the irradiated cell cultures to which the compound suspected of protecting against the formation of x-ray-induced DNA lesions was added, as compared to the frequency of chromatid breaks present in the irradiated cell cultures to which the compound suspected of protecting against the formation of x-ray-induced DNA lesions was not added;

wherein a significant decrease indicates that the compound which is suspected of protecting against the formation of x-ray-induced DNA lesions does protect against the formation of x-ray induced DNA lesions.

31. The process of claim 30 wherein ara-C is added 10 min to 30 min after the cell cultures are irradiated.

32. The process of claim 30 wherein cell division is arrested 0.5 to 1.5 hours after the cells are irradiated.

33. The process of claim 30 wherein the cell cultures comprise skin fibroblasts or peripheral blood lymphocytes.

34. The process of claim 33 wherein 50 $\mu$M ara-C is added.

* * * * *

UNITED STATES PATENT AND TRADEMARK OFFICE
CERTIFICATE OF CORRECTION

PATENT NO. : 6,017,706
DATED : January 25, 2000
INVENTOR(S) : Ram Parshad et al

Page 1 of 1

It is certified that error appears in the above-identified patent and that said Letters Patent is hereby corrected as shown below:

On the cover page, after "[22] Filed: May 7, 1997", delete " Related U.S. Application Data [63] Continuation-in-part of aplication No. 08/611,330, Mar. 8, 1996, Pat. No. 5,773,219 which is a continuation-in-part of application No. 08/228,825, Apr. 18, 1994, abandoned, which is a continuation-in-part of appliaction No. 07/957,315, Oct. 6, 1992, Abandoned."

Column 1,
Line 7, delete "RELATED APPLICATIONS".

Column 1,
Lines 8-15, delete "This application is a continuation-in-part of U.S. application Ser. No. 08/611,330, filed Mar. 8, 1996, which issued as U.S. Pat. No. 5,773,219 on Jun. 30, 1998, which application is in turn a continuation in part of U.S. application Ser. No. 08/228,825, filed Apr.18, 1994, now abandoned which is in turn a continuation-in-part of U.S. application Ser. No. 07/957,315, filed Oct. 6, 1992, now abandoned.".

Signed and Sealed this

Twelfth Day of June, 2001

*Attest:*

Nicholas P. Godici

*Attesting Officer*

NICHOLAS P. GODICI
*Acting Director of the United States Patent and Trademark Office*